United States Patent [19]

Kurosaki et al.

[11] Patent Number: 4,623,743
[45] Date of Patent: Nov. 18, 1986

[54] PHOSPHORIC ESTERS AND METHOD FOR PREPARING THE SAME

[75] Inventors: Tomihiro Kurosaki, Osaka; Mitsuharu Masuda, Wakayama, both of Japan

[73] Assignee: Kao Corporation, Tokyo, Japan

[21] Appl. No.: 700,033

[22] Filed: Feb. 11, 1985

[30] Foreign Application Priority Data

Jan. 3, 1984 [JP] Japan ................................. 59-39042

[51] Int. Cl.$^4$ ............................................... C07F 9/09
[52] U.S. Cl. ..................................... 558/105; 558/169
[58] Field of Search ................ 260/925, 978; 558/105, 558/169

[56] References Cited

U.S. PATENT DOCUMENTS 3,304,349  2/1967  Shen ..................................... 260/920
3,507,937  4/1970  Zimmerer ........................... 260/948
4,372,809  2/1983  Lindemann et al. ................ 260/945

OTHER PUBLICATIONS

Kao Soap, Abstract of Jpn. Kokai Tokkyo Koho Japan 57,163,305, 10/12/82, CA. 98:107549m (1983).

Primary Examiner—Anton H. Sutto
Attorney, Agent, or Firm—Oblon, Fisher, Spivak, McClelland & Maier

[57] ABSTRACT

A phosphoric ester of the following formula (I):

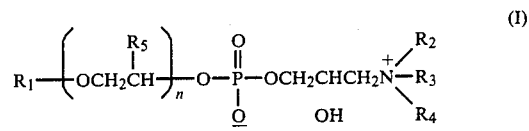

in which $R_1$ represents a saturated or unsaturated, linear or branched and substituted or unsubstituted hydrocarbon group having from 8 to 32 carbon atoms, $R_2$, $R_3$ and $R_4$ are the same or different and represent a saturated or unsaturated hydrocarbon group having from 1 to 4 carbon atoms, $R_5$ represents a hydrogen atom, a saturated or unsaturated hydrocarbon group having from 1 to 4 carbon atoms, and n is an integer of from 0 to 50.

The above novel phosphoric acid ester has excellent detergent performance with very low irritations to living body.

A manufacturing method of the ester is also disclosed. According to the method, the ester can be prepared from inexpensive, readily available starting materials by a simple procedure in high purity and high yield.

2 Claims, 1 Drawing Figure

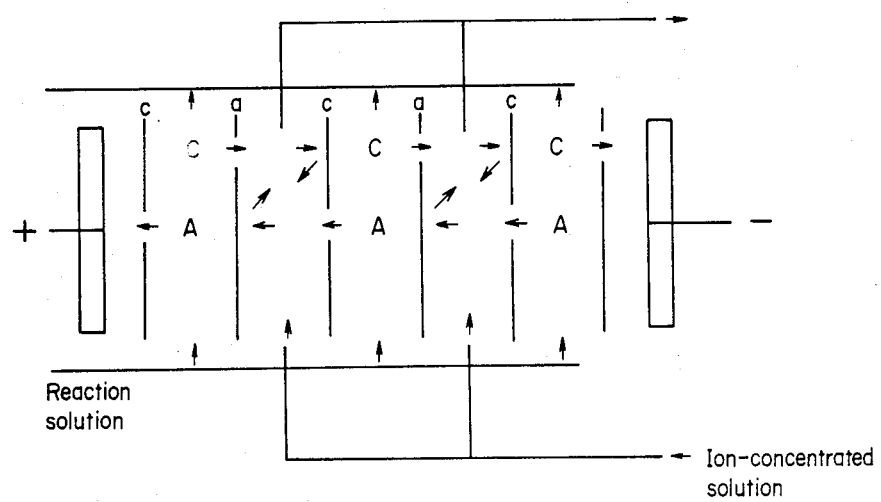

PHOSPHORIC ESTERS AND METHOD FOR PREPARING THE SAME

BACKGROUND OF THE INVENTION (i) Field of the Invention

This invention relates to novel phosphoric esters and more particularly, to phosphoric esters of the general formula (I)

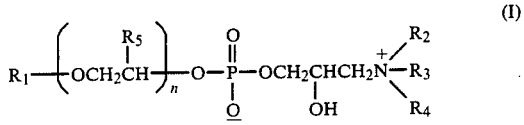

in which $R_1$ represents a saturated or unsaturated, linear or branched and substituted or unsubstituted hydrocarbon group having from 8 to 32 carbon atoms, $R_2$, $R_3$ and $R_4$ are the same or different and represent a saturated or unsaturated hydrocarbon group having from 1 to 4 carbon atoms, $R_5$ represents a hydrogen atom a saturated or unsaturated hydrocarbon group having from 1 to 4 carbon atoms, and n is an integer of from 0 to 56.5.

The invention also relates to a method for preparing the phosphoric acids of the type indicated above.

(ii) Description of the Prior Art

As phosphoric esters having quaternary ammonium salts in one molecule thereof, there are known phospholipids, typical of which is natural lecithin. These phospholipids have surface activity, emulsifiability and physiological characteristics and are thus used in various fields.

A number of substances are currently used as detergents, including alkylsulfates, polyoxyethylene alkylsulfates, alkylbenzenesulfonates, alphaolefinsulfonates, monoalkyl phosphates, acylglutamic acid salts, and the like. These surface active agents, in most cases, bring about chapping of skin. For the purpose of low skin irritations, there are now used monoalkyl phosphates and acylglutamic acid salts.

As is well known, a number of phosphoric ester derivatives such as phospholipids exist in living body, so that it will be expected that substances having structures similar to those of phosphoric ester derivatives, e.g. phosphoric esters having quaternary ammonium salts in one molecule thereof, have low irritations against living body.

However, it is usually very difficult to prepare phospholipids: the preparation generally needs a number of steps, resulting in a low yield of an intended product (see, for example, E. Baer et al; J. Amer. Chem. Soc. 72, 942(1950), and "Lipids" edited by Tamio Yamakawa and published by Kyoritsu Pub. Co., Ltd. (1973)).

The results of several studies on synthesis of compounds having structures similar to those structures of phospholipids have been reported. However, these reactions comprise a number of complicate steps, or may, in some cases, need starting materials which are difficult to prepare. Alternatively, an intended product obtained after the reaction may often be very difficult to separate and yield of which is low. In addition, final products have not necessarily adequate surface activity (see, for example, Japanese Patent Publication Nos. 42-23330 and 48-1654, and U.S. Pat. No. 3507937).

SUMMARY OF THE INVENTION

Under these circumstances, the present inventors made intensive studies and, as a result, found that novel phosphoric esters of the formula (I) which could be prepared from inexpensive, readily available starting materials by a simple procedure in high purity and high yield had good detergent action and very low irritations against living body. The present invention is accomplished on the basis of the above finding.

It is accordingly an object of the invention to provide novel phosphoric esters of the general formula (I).

It is another object of the invention to provide a novel method for preparing phosphoric esters of the formula (I).

BRIEF DESCRIPTION OF THE INVENTION

A sole FIGURE is a schematic view of an electrodialyzer using for purification in the method of the invention.

A: anion, C: cation, a: anion-exchange membrane, c: cation-exchange membrane.

DETAILED DESCRIPTION OF THE INVENTION AND PREFERRED EMBODIMENTS

In the formula (I) showing the phosphoric esters of the invention, $R_1$ represents a saturated or unsaturated, linear or branched hydrocarbon group having from 8 to 32 carbon atoms. Examples of the hydrocarbon group include octyl, nonyl, decyl, dodecyl, undecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacocyl, heptacosyl, octacosyl, nonacosyl, triacontyl, hentriacontyl, dotriacontyl, octenyl, nonenyl, decenyl, dodecenyl, undecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, pentacocenyl, hexacocenyl, heptacocenyl, octococenyl, nonacocenyl, triacontenyl, hentriacontenyl, dotriacontenyl, octadienyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, eicosadienyl, heneicosadienyl, docosadienyl, tricosadienyl, tetracosadienyl, pentacosadienyl, hexacosadienyl, heptacosadienyl, octacosadienyl, nonacosadienyl, triacontadienyl, hentriacontadienyl, dotriacontadienyl, 2-hexyldecyl, 2-octylundecyl, 2-decyltetradecyl, 2-undecylhexadecyl, 2-tetradecyloctadecyl, and the like. These hydrocarbon groups may be substituted with a substituent. Examples of such substituent include halogen, nitro, amino, phenyl, hydroxyl, and the like. The saturated or unsaturated hydrocarbon groups having from 1 to 4 carbon atoms and represented by $R_2$, $R_3$ and $R_4$ include, for example, methyl, ethyl, propyl, butyl, ethenyl, propenyl, butenyl, butadienyl, ethynyl, propynyl, butynyl, butadinyl, and the like.

The phosphoric esters (I) of the present invention are prepared, for example, by interacting phosphoric monoesters (II) and glycidyl trialkylammonium salts (III) according to the following formula

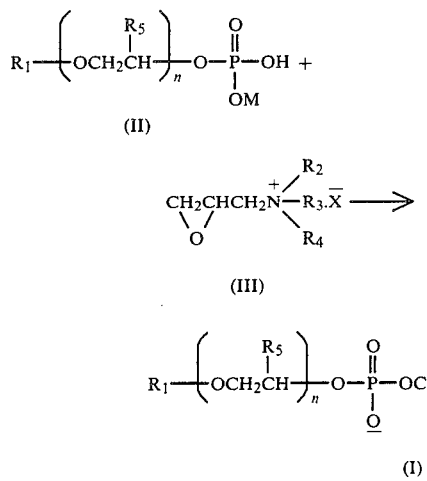

in which M represents an alkali metal, X represents an anion, and $R_1$, $R_2$, $R_3$, $R_4$, $R_5$ and n have, respectively, the same meanings as defined before.

The anion represented by X in the formula (III) includes, for example, chlorine, bromine or the like.

In order to carry out the method of the invention, a phosphoric monoester of the formula (II) is reacted with a glycidyl trialkylammonium salt of the formula (III) used in an amount of 1 to 10 times by mole, preferably 1 to 5 times by mole, the phosphoric monoester. The reaction is effected in the presence or absence of an inert solvent at a temperature of from 30° to 150° C., preferably 40° to 90° C. Examples of the inert solvents include polar solvents such as water, methanol, ethanol, isopropanol and the like.

The reaction product usually comprises, aside from the novel phosphoric ester of the general formula (I) to which the present invention is directed, inorganic salts, unreacted phosphate and glycidyl trialkylammonium salt, and ring-opened epoxy products thereof. The ratios of the respective substances in the reaction product depend on the types of phosphoric monoester and glycidyl trialkylammonium salt, the molar ratio of the starting materials, the type and amount to solvent used, and the reaction conditions such as reaction temperature.

The reaction product may be used as it is, depending on the purpose in end use. However, if a product with a high purity is desired, the reaction product may be purified by an electrodialysis using an ion-exchange membrane and developed by us, thereby obtaining a phosphoric ester (I) having a purity as high as over 99%. More specifically, when ionic compounds are removed from the reaction product using an electrical technique which makes use of commercially available ion-exchange membranes including, for example, cation exchange membranes such as C66-5T (Tokuyama Soda Co., Ltd.), CMV (Asahi Glass Co., Ltd.) and the like, anion exchange membranes such as ACH-45T (Tokuyama Soda Co., Ltd.) AMV (Asahi Glass Co., Ltd.) and the like, the amphoteric phosphoric ester (I) alone is left and other impurities are removed from the reaction product. Removal of water from the residue by distillation results in the phosphoric ester with a high purity.

The phosphoric ester (I) of the present invention which is obtained as described above has good surface tension, a high degree of frothing, and very low irritations against the skin and can be used in detergent compositions, cosmetic compositions, emulsifiers, dispersants, antistatic agents and the like.

The present invention is described by way of examples and test examples.

Example 1

Five hundreds parts by weight of monolauryl phosphate was charged into a reactor, to which was added 1950 parts by weight of 1N potassium hydroxide aqueous solution, followed by agitation and heating to 60° C. to obtain a uniform solution. Subsequently, while the reaction system was kept at around 60° C., a solution of 1390 parts by weight of glycidyl trimethylammonium chloride dissolved in 750 parts by weight of water was gradually dropped into the solution, followed by reaction at 60° C. for 5 hours. After completion of the reaction, the reaction system was subjected to filtration to remove floating impurities therefrom. The resulting solution was passed through an electrodialyzer (FIGURE) to remove ionic impurities, followed by distilling off water from the reaction solution to obtain a very hygroscopic, white powdery compound. The compound was analyzed with the following results and identified as an intended compound. The purity was found to be over 99%.

Elementary Analysis (wt%): Calculated: C; 56.7, H; 10.6, N; 3.7, P; 8.1. Found: C; 56.6, H; 10.4, N; 3.6, P; 7.4.

Proton NMR (ppm) Solvent: $D_2O$.

δ; 0.6–2.0 (m, 25H); 3.27 (s, 9H); 3.44–4.20 (m, 5H); 4.43 (br, s, 1H).

$C_{13}$-NMR (ppm) Solvent: $D_2O$.

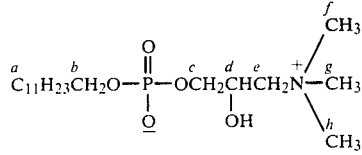

a: 14.13, 22.98, 30.29, 31.19, 32.41
b: 66.35
c: 65.70
d: 65.22
e: 67.49
f,g,h: 54.50

Other analytical values

Acid value (KOH mg/g): 0.73 (by automatic titration method)

Hydroxyl value (KOH mg/g): 151 (by automatic titration method)

Oxirane value (KOH mg/g): −5.7 (by automatic titration method)

Chlorine anion (wt%): 0.01 (by Volhard method)

Total chlorine (wt%): 0.01 (″)

Water content (wt%): 1.77

Example 2

Five hundreds parts by weight of monocetyl phosphate was charged into a reactor, to which was added 1650 parts by weight of 1N potassium hydroxide aqueous solution, followed by agitation and heating to 60° C. to obtain a uniform solution. Subsequently, while the reaction system was kept at around 60° C., a solution of 1170 parts by weight of glycidyl trimethylammonium chloride dissolved in 630 parts by weight of water was gradually dropped into the solution, followed by reaction at 60° C. for 5 hours. After completion of the reaction, the reaction system was subjected to filtration and the resulting solution was passed through an electrodialyzer (FIGURE) to remove ionic impurities, followed by distilling off water from the reaction solution to obtain a very hygroscopic, white crystalline compound. The compound has a purity over 99%.

Elementary Analysis (wt%): Calculated: C; 60.3, H; 11.1, N; 3.2, P; 7.1. Found: C; 60.4, H; 10.9, N; 3.3, P; 6.9.

$^{13}$C-NMR (ppm)  Solvent: D$_2$O.

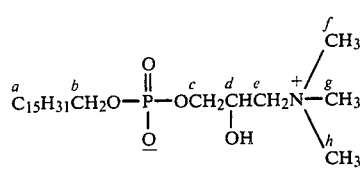

a: 31.92, 30.62, 30.05, 22.74, 14.13
b: 70.66
c: 65.42
d: 65.15
e: 67.32
f,g,h: 54.51
Other analytical values
Acid value (KOH mg/g): 0.51 (by automatic titration method)
Hydroxyl value (KOH mg/g): 128 (by automatic titration method)
Oxirane value (KOH mg/g): −4.1 (by automatic titration method)
Chlorine anion (wt%): 0.02 (by Volhard method)
Total chlorine (wt%): 0.02  (")
Water content (wt%): 1.48

Example 3

Five hundreds parts by weight of monooctyl phosphate was charged into a reactor, to which was added 2520 parts by weight of 1N potassium hydroxide aqueous solution, followed by agitation and heating to 60° C. to obtain a uniform solution. Subsequently, while the reaction system was kept at around 60° C., a solution of 1810 parts by weight of glycidyl trimethylammonium chloride dissolved in 980 parts by weight of water was gradually dropped into the solution, followed by reaction at 60° C. for 5 hours. After completion of the reaction, the reaction system was purified in the same manner as in Examples 1 and 2 to obtain an intended compound. The compound has a purity over 99%.

Elementary Analysis (wt%): Calculated: C; 51.7, H; 9.9, N; 4.3, P; 9.5. Found: C; 51.9, H; 9.8, N; 4.4, P; 9.5

Other analytical values
Acid value (KOH mg/g): 0.21 (by automatic titration method)
Hydroxyl value (KOH mg/g): 181 (by automatic titration method)
Oxirane value (KOH mg/g): −0.34 (by automatic titration method)
Chlorine anion (wt%): 0.03 (by Volhard method)
Total chlorine (wt%): 0.03  (")
Water content (wt%): 1.56

Example 4

Five hundreds parts by weight of 2-octylundecyl phosphate was charged into a reactor, to which was added 1153 parts by weight of 1N potassium hydroxide aqueous solution, followed by agitation and heating to 60° C. to obtain a uniform solution. Subsequently, while the reaction system was kept at around 60° C., a solution of 875 parts by weight of glycidyl trimethylammonium chloride dissolved in 472 parts by weight of water was gradually dropped into the solution, followed by reaction at 60° C. for 5 hours. After completion of the reaction, the reaction system was purified in the same manner as in Examples 1 and 2 to obtain an intended compound. The compound has a purity over 99%.

Elementary Analysis (wt%): Calculated: C; 65.5, H; 11.7, N; 2.6, P; 5.6. Found: C; 65.5, H; 11.6, N; 2.7, P; 5.4

$^{13}$C-NMR (ppm) Solvent: CD$_3$OD.

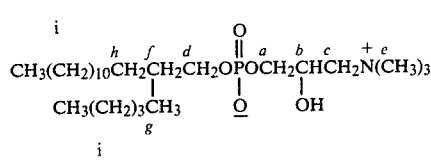

a: 76.99
b: 71.21
c: 70.04
d: 69.00
e: 57.04
f: 38.74
g: 38.25
h: 34.82
i: 29.73

Proton-NMR (ppm)  Solvent: CDCl$_3$.

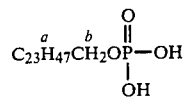

a: 1.2–1.73 (m, 47H)
b: 4.05 (br, s, 1H)
Other analytical values
Acid value (KOH mg/g): 0.25 (by automatic titration method)
Hydroxyl value (KOH mg/g): 102.04 (by automatic titration method)
Oxirane value (KOH mg/g): −0.89 (by automatic titration method)
Chlorine anion (wt%): 0.1 (by Volhard method)
Total chlorine (wt%): 0.1  (")
Water content (wt%): 2.42

Example 5

Five hundreds parts by weight of 2-decyltetradecyl phosphate was charged into a reactor, to which was added 1215 parts by weight of 1N potassium hydroxide aqueous solution, followed by agitation and heating to 60° C. to obtain a uniform solution. Subsequently, while the reaction system was kept at around 60° C., a solution of 880 parts by weight of glycidyl trimethylammonium chloride dissolved in 480 parts by weight of water was gradually dropped into the solution, followed by reaction at 60° C. for 5 hours. After completion of the reaction, the reaction system was treated in the same manner as in Examples 1 and 2 to obtain an intended compound. The compound has a purity over 99%.

Elementary Analysis (wt%): Calculated: C; 56.2, H; 11.7, N; 2.5, P; 5.6. Found: C; 56.0, H; 11.7, N; 2.7, P; 5.4.

Other analytical values
Acid value (KOH mg/g): 0.23 (by automatic titration method)
Hydroxyl value (KOH mg/g): 102 (by automatic titration method)
Oxirane value (KOH mg/g): −0.89 (by automatic titration method)
Chlorine anion (wt%): 0.01 (by Volhard method)
Total chlorine (wt%): 0.01 (")
Water content (wt%): 2.21

Example 6

Five hundreds parts by weight of trioxyethylene lauryl ether phosphate was charged into a reactor, to which was added 1325 parts by weight of 1N potassium hydroxide aqueous solution, followed by agitation and heating to 60° C. to obtain a uniform solution. Subsequently, while the reaction system was kept at around 60° C., a solution of 950 parts by weight of glycidyl trimethylammonium chloride dissolved in 515 parts by weight of water was gradually dropped into the solution, followed by reaction at 60° C. for 5 hours. After completion of the reaction, the reaction system was treated in the same manner as in Examples 1 and 2 to obtain an intended compound. The compound has a purity over 99%.

Elementary Analysis (wt%): Calculated: C; 56.2, H; 10.2, N; 2.7, P; 6.0. Found: 56.3, H; 10.0, N; 2.7, P; 5.9.
Other analytical values
Acid value (KOH mg/g): 0.14 (by automatic titration method)
Hydroxyl value (KOH mg/g): 109 (by automatic titration method)
Oxirane value (KOH mg/g): −0.48 (by automatic titration method)
Chlorine anion (wt%): 0.02 (by Volhard method)
Total chlorine (wt%): 0.02 (")
Water content (wt%): 1.85

Example 7

Five hundreds parts by weight of eicosyloxyethylene lauryl ether phosphate was charged into a reactor, to which was added 210 parts by weight of 1N potassium hydroxide aqueous solution, followed by agitation and heating to 60° C. to obtain a uniform solution. Subsequently, a solution of 330 parts by weight of glycidyl trimethylammonium chloride dissolved in 180 parts by weight of water was gradually dropped into the solution, followed by reaction at 60° C. for 5 hours. Therefore, the reaction system was treated in the same manner as in Examples 1 and 2 to obtain an intended compound. The compound was a purity over 99%.

Elementary Analysis (wt%): Calculated: C; 55.1, H; 9.6, N; 1.1, P; 2.5. Found: C; 55.0, H; 9.6, N; 1.1, P; 2.3.
Other analytical values
Acid value (KOH mg/g): 0.08 (by automatic titration method)
Hydroxyl value (KOH mg/g): 44 (by automatic titration method)
Oxirane value (KOH mg/g): −0.09 (by automatic titration method)
Chlorine anion (wt%): 0.01 (by Volhard method)
Total chlorine (wt%): 0.01 (")
Water content (wt%): 2.21

Example 8

Five hundreds parts by weight of polyoxyethylene polyoxypropylene octyl ether phosphate (adduct of 7.5 moles of ethylene oxide and 49 moles of propylene oxide) was charged into a reactor, to which was added 208 parts by weight of 1N potassium hydroxide aqueous solution, followed by agitation and heating to 60° C. to obtain a uniform solution. Subsequently, a solution of 151 parts by weight of glycidyl trimethylammonium chloride dissolved in 81 parts by weight of water was gradually dropped into the solution, followed by reaction at 60° C. for 5 hours. Thereafter, the reaction system was treated in the same manner as in Examples 1 and 2 to obtain an intended compound. The compound has a purity over 99%.

Elementary Analysis (wt%): Calculated: C; 60.4, H; 9.6, N; 0.4, P; 0.9. Found: C; 60.3, H; 9.5, N; 0.3, P; 0.8.
Other analytical values
Acid value (KOH mg/g): 0.01 (by automatic titration method)
Hydroxyl value (KOH mg/g): 16 (by automatic titration method)
Oxirane value (KOH mg/g): −0.89 (by automatic titration method)
Chlorine anion (wt%): 0.01 (by Volhard method)
Total chlorine (wt%): 0.01 (")
Water content (wt%): 2.15

Test 1

The compound obtained in Example 1 was evaluated using a 10% aqueous solution thereof as follows: a 24 hours closed patch test was carried out using the skin on the back of guinea pig to assess irritations against the skin as an average value of five guinea pigs used as one group.

The skin irritations were evaluated in terms of an intensity of the skin reaction a certain time after removal of the patch as follows:

|  | Evaluation point |
|---|---|
| (−): no reaction | 0 |
| (±): slight red spots | 0.5 |
| (+): clear red spots | 1 |
| (++): red spots with edemata | 2 |
| (+++): scabs or necrosis recognized in the red spots or edemata | 3 |

For comparison, 1-sodium salt of monolauryl phosphate was used among monoalkyl phosphates which were accepted as being less skin irritative. However, when the sodium salt was used in a such a high concentration as 10%, an appreciable irritation reaction took place. It will be noted that with monoalkyl phosphates, no irritation reaction took place up to a concentration of 5%, and with lauryl sulfates which are typical of ordinary anionic surface active agents, the irritation reaction is recognized in a concentration as low as 0.5% and an intensive irritation reaction occurs in a concentration of 2%.

The results are shown in Table 1 below.

TABLE 1

| Compound | Evaluation Point of Skin Irritations (on average) | | |
|---|---|---|---|
|  | after 3 hrs. | after 24 hrs. | after 48 hrs. |
| Compounds obtained in Example 1 | 1.3 | 1.2 | 1.1 |
| 1-Sodium Salt of Monolauryl Phosphate | 1.8 | 2.6 | 3.0 |

Test 2

A liquid skin detergent having the following formulation was prepared. The detergent was weakly acidic in nature and when used for washing the face, it served to fully clean the face and involved no stretching of the face after the washing.

| Liquid skin detergent (pH 5.6) | |
| --- | --- |
| $C_{12}$ phosphobetaine (compound of Example 1) | 25.0 (wt %) |
| Miranol 2CM (amphoteric surface active agent, by Miranol Co., Ltd.) | 5.0 |
| Glycerine | 10.0 |
| Carboxyvinyl polymer | 0.6 |
| Potassium hydroxide | 0.16 |
| Perfume, colorant, preservative | suitable amount |
| Deionized water | balance |
| | 100 |

Test 3

An oil-in-water type skin cream having the following formulation was prepared. The cream was neutral to weakly acidic in nature and was well emulsified. The cream was free of stickiness and had good affinity for the skin.

| Oil-in-water type skin cream: | |
| --- | --- |
| $C_{16}$ phosphobetaine (compound of Example 2) | 1.2 (wt %) |
| Glycerine monostearate | 2.4 |
| Cetanol | 4.0 |
| Solid paraffin | 5.0 |
| Squalane | 10.0 |
| Octadodecyl meyristate | 6.0 |
| Glycerine | 6.0 |
| Perfume, colorant, preservative | suitable amounts |
| Deionized water | balance |
| | 100.0 |

What is claimed is:

1. A phosphoric ester of the following general formula (I)

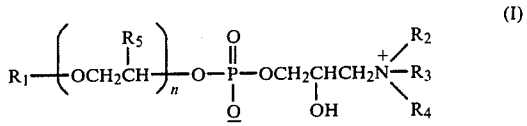

which $R_1$ represents a saturated or unsaturated, linear or branched and substituted or unsubstituted hydrocarbon group having from 8 to 32 carbon atoms, $R_2$, $R_3$ and $R_4$ are the same or different and represent a saturated or unsaturated hydrocarbon group having from 1 to 4 carbon atoms, $R_5$ represents a hydrogen atom a saturated or unsaturated hydrocarbon group having from 1 to 4 carbon atoms, and n is an integer of from 0 to 56.5.

2. Method for preparing a phosphoric acid of the general formula (I)

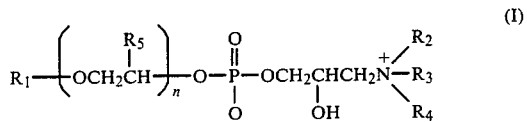

in which $R_1$ represents a hydrogen atom a saturated or unsaturated, liner or branched and substituted or unsubstituted hydrocarbon group having from 8 to 32 carbon atoms, $R_2$, $R_3$ and $R_4$ are the same or different and represents a saturated or unsaturated hydrocarbon group having from 1 to 4 carbon atoms, $R_5$ represents a saturated or unsaturated hydrocarbon group having from 1 to 4 carbon atoms, and n is an integer of from 0 to 56.5, characterized by interacting a phosphoric monoester of the general formula (II)

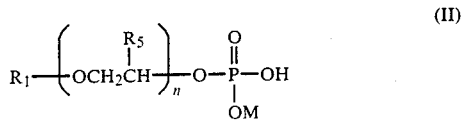

in which $R_1$, $R_5$ and n have the same meanings as defined above, respectively, and M represents an alkali metal, and a glycidyl trialkylammonium salt of the general formula (III)

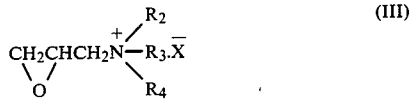

in which $R_2$, $R_3$ and $R_4$ have, respectively, the same meanings as defined above, and X represents an anion.

* * * * *